United States Patent

Griengl et al.

[11] 4,256,764
[45] Mar. 17, 1981

[54] PROCESS FOR MAKING DERIVATIVES OF DIMERS OF ISOEUGENOL

[75] Inventors: Herfried Griengl; Gabriele Foidl, both of Graz, Austria

[73] Assignee: PLC Pharmaceutical Licenses Co. Ltd., Switzerland

[21] Appl. No.: 80,552

[22] Filed: Oct. 1, 1979

[30] Foreign Application Priority Data

Nov. 15, 1978 [AT] Austria .................. 8151/78

[51] Int. Cl.³ ............ A61K 31/34; C07D 307/86
[52] U.S. Cl. .................. 424/285; 424/330; 260/346.73; 564/387
[58] Field of Search .............. 260/346.73; 424/285

[56] References Cited

PUBLICATIONS

Petrov et al., J. Chem. Abstracts, vol. 52, 9074i,(1958).

Primary Examiner—Henry R. Jiles
Assistant Examiner—Bernard Dentz
Attorney, Agent, or Firm—Stevens, Davis, Miller & Mosher

[57] ABSTRACT

Compounds of formula

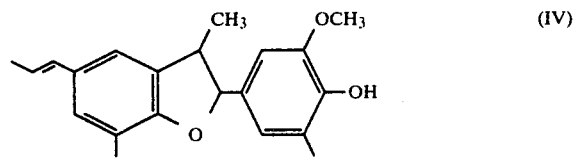

and

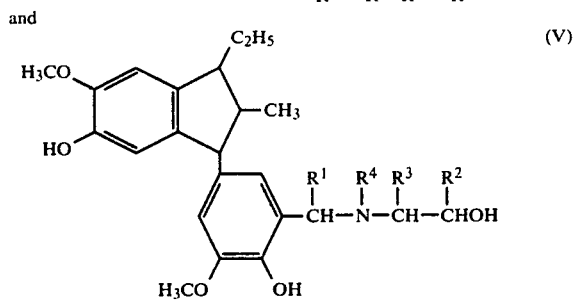

have liver-protecting properties. They are prepared by reacting dehydro-isoeugenol or di-isoeugenol with an oxazolidine of formula

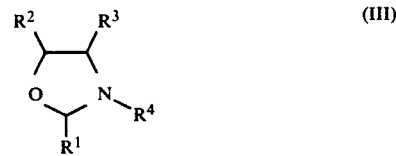

7 Claims, No Drawings

PROCESS FOR MAKING DERIVATIVES OF DIMERS OF ISOEUGENOL

The invention relates to a process for making to some extent new water-soluble derivatives of dimers of isoeugenol. (E) - isoeugenol is converted on mild oxidation, for example with, iron (III) chloride into a dimeric, trans-2,3-dihydro-2-(4-hydroxy-3-methoxyphenyl)-7-methoxy-3-methyl-5-(E)-propenylbenzofurane ("dehydrodiisoeugenol"), as described for the first time by H. Erdtman in the Biochemische Zeitschrift, volume 258 in the year 1933 on pages 172 to 180.

However, in the acid medium a dimer of different structure, is formed: i.e. (1α, 2β, 3α)-1-ethyl-3-(4-hydroxy-methoxyphenyl)-6-methoxy-2-methyl-5-indanol ("diisoeugenol") is formed. This was observed for the first time by E. Puxeddu and published in the Gazzetta Chimica Italiana in the year 1909, pages 131 to 137.

Both dimers have valuable properties as active substances on treatment of liver diseases, as described below for example in the case of "dehydrodiisoeugenol":

A standard testing process for pharmacological effect for experimental liver damage is the hexobarbitone sleep test, whose execution is described among others in a work by G. Vogel et al. in the Arzneimittelforschung, volume 25 (1975), pp. 82–89 and pp. 179–188. For this purpose 100 mg/kg of the compound to be tested were given to rats in groups each of 15 animals in carboxymethyl cellulose intraperitoneally and 90 minutes later 0.3 ml/kg carbon tetrachloride in olive oil by means of a throat probe. The rats were anaesthetised 48 hours later by intraperitoneal dosing of 70 mg/kg of hexabarbitone and the sleep duration was determined:

|  | min |
| --- | --- |
| Carbon tetrachloride without test compound | 128 |
| control (only hexobarbitone) | 83 |
| trans-2,3-dihydro-2-(4-hydroxy-3-methoxy-phenyl)-7-methoxy-3-methyl-5-(E)-propenylbenzofurane ("dehydrodiisoeugenol") | 97 |
| Silymarin | 115 |

The effect of the trans-2,3-dihydro-2-(4-hydroxy-3-methoxy-phenyl)-7-methoxy-3-methyl-5-(E)-propenyl-benzofurane ("dehydrodiisoeugenol") is highly significant (p<0.01); that of the reference compound Silymarin, a well-known liver medicament, is statistically not significant.

A great disadvantage with reference to the application range width of the described dimers of the isoeugenol is, however, their low water solubility. It is possible to convert these dimers with formaldehyde and by means of a secondary amine in a conventional manner into the corresponding Mannich bases; however, the yields are poor and it is difficult to separate the nonconverted formaldehyde from the reaction products.

The objective of the invention is to produce easily water-soluble derivatives of dimers of isoeugenol which can be produced with good yield and whose medical effects correspond to that of the initial materials. This objective is achieved by the invention.

The objective of the invention is a new process which makes it possible to produce N-alkyl-N-(2-hydroxyalkyl) aminomethyl derivatives of dimers of isoeugenol with excellent yield using simple reactions. The principle of the new process is that a dimer of isoeugenol with the formula

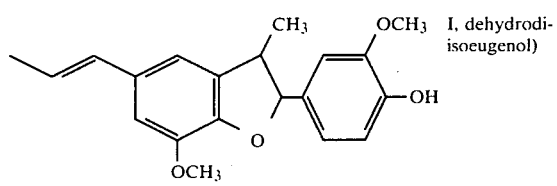

(I, dehydrodiisoeugenol)

or with the formula

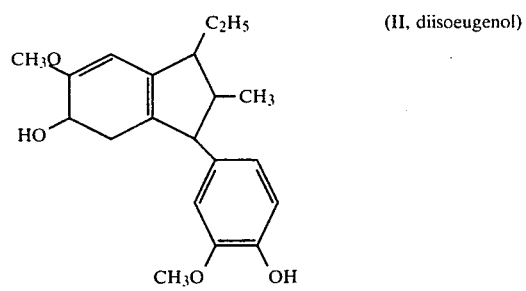

(II, diisoeugenol)

is converted with an oxazolidine of the general formula (III)

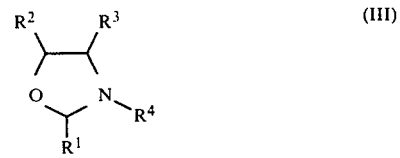

in which:

R1 represents preferably hydrogen, however, also a branched or nonbranched alkyl radical with one to four carbon atoms, especially an isopropyl group, but not a tertiary butyl group, or halogen substituted, especially chlorine, but preferably nonsubstituted phenyl radical R2 represents hydrogen or a phenyl residue.

R3 represents hydrogen or a methyl group.

R4 represents a branched or nonbranched alkyl group with one to four carbon atoms which can support as substituent a hydroxy group, preferably a methyl, ethyl, 2-hydroxyethyl, propyl, isopropyl, butyl or tertiary butyl group, an allyl group or a benzyl group in which compounds of general formula (IV)

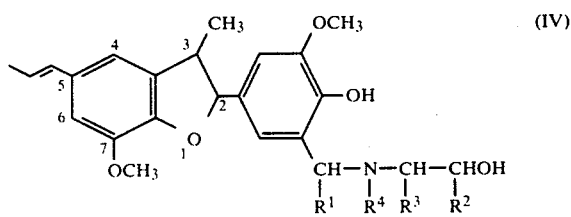

or compounds of the general formula (V)

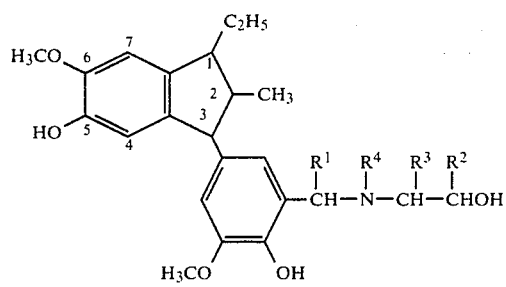

are produced, in which R1, R2, R3, R4 have the same meaning as in the compounds of the general formula (III).

On converting the compounds of general formula (IV) and (V) produced by the process according to the invention, with acids into corresponding ammonium salts, which are further below described, it is possible to achieve excellent water solubility, in which the presence of the newly introduced hydrophilic alcoholic hydroxyl group has also a favourable effect. The production of the 1,3-oxazolidine of general formula (III) necessary for conversion is carried out in a conventional manner by condensation of aldehydes of general formula R1-CHO with N-substituted ethanol amine derivatives of general formula

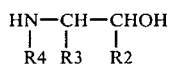

in which R1, R2, R3, and R4 have the same meaning as in the compounds of the general formula (III) and as described for example by E. D. Bergmann, E. Zimkin and S. Pinchas in the "Recueil des Travaux Chimiques des Pays-Bas" in volume 71 (1952) on page 171. For experimental execution of the process according to the invention there are selected preferably equimolar quantities of "dehydrodiisoeugenol" or "diisoeugenol" and 1,2-oxazolidine or an excess of the latter and it is allowed to react in a suitable solvent at temperatures between room temperature and the boiling temperature of the solvent used, for example at 40° to 80° C., for a few hours up to a few days, preferably from 10 to 60 hours.

Alcohols such as methanol, ethanol or 2-propanol, ethers such as diethyl ether, diisopropyl ether, dioxan or tetrahydrofurane or nitriles such as acetonitrile or propion nitrile can be used as solvents.

The processing is carried out as a rule by evaporation of the solvent in vacuum and recrystallisation or reprecipitation of the residue, if necessary by using a chromatographic purification.

The obtained free bases of the formulae (IV) and (V) can be converted into their ammonium salts, especially their salts with physiologically acceptable acids. Such suitable acids are preferably inorganic acids such as hydrochloric acid, hydrobromic acid, sulphuric acid or phosphoric acid, or organic acids such as formic, acetic, propionic, succinic, glycolic, lactic, malic, tartaric, citric, ethanosulphonic, hydroxy ethanosulphonic, ascorbic, liponic, aspartic, α-ketoglutaric, glutamic, saccharic, gluconic, mucic or thiazolidine carbonic acid. Formation of the salts is carried out for example by conversion of the acid with the free base of the formula (IV) or (V), usefully in a suitable solvent, such as one of those given above.

Owing to the close relationships between the free compound and the salt when one is named, within the same meaning the others are also to be understood.

The compounds produced by the process according to the invention and which are partly new, possess valuable medical properties, especially protection against liver damage. Hence for example on taking orally in quantities of 20 to 500 mg/kg to rats in the galactosamine test a marked liver protecting effect has been observed and on intravenous application in quantities of 10 to 300 mg/kg to mice in the α amanitine tests a marked mortality-reducing effect was observed.

These tests have been described in the already-quoted work by G. Vogel et al. published in Arzneimittelforschung, volume 25 (1975), pages 82 to 89 and 179 to 188.

In the galactosamine tests the rats received in groups each of 15 animals 100 mg/kg of the compound to be tested N-(5-(trans-2,3-dihydro-7-methoxy-3-methyl-5-(E)-propenylbenzofuran-2-yl)-2-hydroxy-3-methoxyphenylmethyl)-N-(2-hydroxyethyl)-N-methyl-ammonium chloride and for comparison purposes Silymarine in the tragacanth suspension perorally, one hour later interperitoneally 350 mg/kg of galactosamine hydrochloride and 24 hours later blood samples were taken for determining the serum enzymes GOT and GPT.

| | GOT | GPT |
|---|---|---|
| Galactosamine hydrochloride without test compound | 572 | 578 |
| control | 113 | 53 |
| N-(5-(trans-2,3-dihydro-7 methoxy-3-methyl-5-(E)-propenylbenzofuran-2-yl)-2-hydroxy-3-methoxy phenylmethyl)-N-(2-hydroxyethyl-N-methyl ammonium cloride | 422 | 185 |
| Silymarine | 794 | 225 |

Especially in the case of enzyme GPT the effect of the tested new compound was highly significant (p<0.01) and clearly better than that of Silymarine.

In the α amanitine test the mice received in groups of 20 animals each 50 mg/kg of N-(5-(trans-2,3-dihydro-7-methoxy-3-methyl-5-(E)-propenyl benzofuran-2-yl)-2--hydroxy-3-methoxyphenyl-methyl)-N) (2-hydroxyethyl)-N-methyl ammonium chloride and for comparison Silymarine intravenously and an hour later 0.7 mg/kg of α amanitine intraperitoneally. The mortality variation was observed for 7 days. Silymarine did not cause any reduction of the mortality cases in comparison with that of the control group; in case of N-(5-trans-2,3-dihydro-7-methoxy-3-methyl-5-(E)-propenylbenzofurane-2-yl)-2-hydroxy-3-methoxyphenylmethyl)-N-(2-hydroxyethyl)-N-methyl ammonium chloride the mortality rate was only 20%.

The toxicologic investigations indicate a good compatibility of the compounds produced by the process according to the invention. Hence for example the LD50 in case of rats after peroral application is for N-(5-(trans-2,3-dihydro-7-methoxy-3-methyl-5-(E)-propenyl-benzofuran-2-yl)-2-hydroxy-3-methoxyphenylmethyl)-N-(2-hydroxyethyl)-N-methyl ammonium chloride between 4 and 16 mg/kg.

The medical preparations containing new compounds are hence valuable healing means for treatment of liver damage and for its prevention.

The medically active compounds made by the process according to the invention and which are partly new, can be used in the form of medical preparations, which contain them in free form or in the form of their salts, especially the therapeutically used salts in mixtures with suitable pharmaceutical inorganic or organic, solid, or liquid carrier materials suitable for enteral or parenteral application. For the formation of this preparations can be considered for those materials which do not react with the active substance, such as for example water, gelatine, lactose, starch, tragacanth, stearyl alcohol, magnesium stearate, talcum powder, vegetable oils, benzyl alcohols, propylene glycol, vaseline and other known medical carrier substances. The pharmaceutical preparations can be made for example as tablets, pellets, capsules, suppositories or in liquid form as solutions (for example liquors or syrups), suspensions or emulsions. If necessary they are sterilised and/or contain secondary substances such as preservatives, stabilisers, wetting or emulsifying agents, solubilizers or salts for changing the osmotic pressure or buffers. They can contain also other therapeutically valuable substances. The pharmaceutical preparations are made by conventional methods.

EXAMPLE 1

20.0 g of trans-2,3-dihydro-2-(4-hydroxy-3-methoxyphenyl)-7-methoxy-3-methyl-5-(E)-propenylbenzofurane and 16.0 g of 3-methyl-1,3-oxazolidine are held in 120 ml ethanol for 30 hours at 60° C. and subsequently the solvent and excess 3-methyl-1,3-oxazolidine are removed, finally in vacuum. The remaining residue is crystallised out of methylene chloride/petroleum ether and it yields 19.8 g of N-(5(trans-2,3-dihydro-7-methoxy-3-methyl-5-(E)-propenylbenzofuran-2-yl)-2-hydroxy-3-methoxyphenyl methyl)-N-(2-hydroxyethyl)-N-methylamine, fine colourless crystals, melting point 101°–103° C. (destruction)

$C_{24}H_{31}NO_5$ (413.31) Reported: C 69.68; H 7.58; N 3.39. Found: C 69.51; H 7.59; N 3.27.

hydrochloride (by means of ethereal hydrochloric acid): fine faintly yellow.

hygroscopic crystals, melting point 74° C. (destruction).

$C_{24}H_{33}NO_5$ (415.33) Reported: C 69.34; H 8.03; N 3.37. Found: C 69.13; H 7.97; N 3.31.

EXAMPLE 2

20.0 g of (1α, 2β, 3α)-1-ethyl-3-(4-hydroxy-3-methoxy-phenyl)-6-methoxy-2-methyl-5-indanol and 21.6 g of 3-methyl-1,3-oxazolidine are held in 280 ml of absolute alcohol for 36 hours at 60° C. and subsequently the solvent and excess 3-methyl-1,3-oxazolidine are removed, finally in vacuum. After purification by means of a chromatographic column there is obtained 13.6 g of N-(5-((1α, 2β, 3α)-1-ethyl-5-hydroxy-6-methoxy-2-methylindan-3-yl)-2-hydroxy-3-methoxyphenyl methyl)-N-(2-hydroxyethyl-N-methyl amine which are colourless crystals, melting point 141°–143° C.

$C_{24}H_{33}NO_5$ (415.33) Reported: C 69.34; H 8.03; N 3.37. Found: C 69.13; H 7.97; N 3.31.

EXAMPLE 3

20.0 g of trans-2,3-dihydro-2-(4-hydroxy-3-methoxyphenyl)-7-methoxy-3-methyl-5-(E)-propenylbenzofurane and 14.4 g of N-(2-hydroxy-ethyl)-1,3-oxazolidine are held in 240 ml absolute ethanol for 48 hours at 70° C. and subsequently the solvent and excess N-(2-hydroxyethyl)-1,3-oxazolidine are removed, finally in vacuum. Digesting of the residue with diethyl ether yields 14.2 g of N-(5-trans-2,3-dihydro-7-methoxy-3-methyl-5-(E)-propenyl-benzofuran-2-yl)-2-hydroxy-3-methoxyphenyl-methyl)-N,N-bis (2-hydroxyethyl) amine, colourless crystals, melting point 107° C.

$C_{25}H_{33}NO_6$ (443.33) Reported: C 67.67; H 7.52; N 3.16. Found: C 67.35; H 7.61; N 3.22.

EXAMPLE 4

20.0 g of trans-2,3-dihydro-2-(4-hydroxy-3-methoxyphenyl)-7-methoxy-3-methyl-5-(E)-propenylbenzofurane and 20.0 g of 3-benyl-1,3-oxazolidine are held in 200 ml of absolute ethanol for 48 hours at 70° C. and subsequently solvent and excess 3-benzyl-1,3-oxazolidine are removed, finally in vacuum. After purification by means of a chromatographic column there is obtained 17.2 g of N-(5-(trans-2,3-dihydro-7-methoxy-3-methyl-5-(E)-propenyl-benzofuran-2-yl)-2-hydroxy-3-methoxy-phenylmethyl)-N-(2-hydroxyethyl)-N-benzylamine, a colourless oil, which solidifies in the manner of glass at oil pump vacuum.

$C_{30}H_{35}NO_5$ (489.37) Reported: C 73.56; H 7.22; N 2.86. Found: C 73.02; H 7.31; N 2.57.

Hydrochloride (by means of ethereal hydrochloric acid): fine bright yellow.

hygroscopic crystals, melting point 70° C. (destruction).

$C_{30}H_{36}ClNO_5$ (525.82) Reported: C 68.46; H 6.92; N 2.66; Cl 6.74. Found: C 68.73; H 6.96; N 2.47; Cl 6.88.

EXAMPLE 5

20.0 g of Cl α, 2β, 3α)-1-ethyl-3-(4-hydroxy-3-methoxy-phenyl)-6-methoxy-2-methyl-5-indanol and 23.4 g of 3-butyl-1,3-oxazolidine are held in 250 ml of absolute alcohol for 48 hours at 65° C. and subsequently the solvent and excess 3-butyl-1,3-oxazolidine are removed, finally in vacuum. After purification by means of a chromatographic column and crystallisation from $CH_2Cl_2$/benzene there is obtained 14.7 g of N-(5-((1α, 2β, 3α)-1-ethyl-5-hydroxy-6-methoxy-2-methylindan-3-yl)-2-hydroxy-3-methoxyphenylmethyl)-N-(2-hydroxyethyl)-N-butylamine, colourless crystals, melting point 105°–106° C.

$C_{27}H_{39}NO_5$ (457.39) Reported: C 70.84; H 8.61; N 3.06. Found: C 70.88; H 8.75; N 3.01.

EXAMPLE 6

20.0 g of trans-2,3-dihydro-2-(4-hydroxy-3-methoxyphenyl)-7-methoxy-3-methyl-5-(E)-propenylbenzofuran and 32.8 g of 2-(3-chlorophenyl)-3-benzyl-1,3-oxazolidine are held in 260 ml of absolute alcohol for 60 hours at 70° C. and subsequently the solvent and excess of 2-(3-chlorophenyl)-3-benzyl-1,3-oxazolidine are removed, finally in vacuum. After purification by means of a chromatographic column there is obtained 9.8 g of N-(5-(trans-2,3-dihydro-7-methoxy-3-methyl-5-(E)-propenyl-benzofuran-2-yl)-2-hydroxy-3-methoxyphenyl-(3-chlorophenyl)-methyl)-N-(2-hydroxyethyl)-N-benzylamin, a bright yellow oil.

$C_{36}H_{38}ClNO_5$ Reported: C 72.02; H 6.40; N 2.33; Cl 5.91; C 72.68; H 6.57; N 2.23; Cl 5.98.

EXAMPLE 7

20.0 g of trans-2,3-dihydro-2-(4-hydroxy-3-methoxyphenyl)-7-methoxy-3-methyl-5-(E)-propenylbenzofuran and 21.3 g of 3,4-dimethyl-5-phenyl-1,3-oxazolidine are held in 200 ml of absolute alcohol for 60 hours at 70°

C. and subsequently the solvent and excess 3,4-dimethyl-5-phenyl-1,3-oxazolidine are removed, finally in vacuum. After purification by means of a chromatographic column there is obtained 9.1 g of N-(5-(trans-2,3-dihydro-7-methoxy-3-methyl-5-(E)-propenyl-benzofuran-2-yl)-2-hydroxy-3-methoxyphenylmethyl)-N-(1-hydroxy-1-phenyl-2-propyl)-N-methylamin, a yellow oil.

$C_{31}H_{37}NO_5$ (503.37) Reported: C 73.90; H 7.42; N 2.78. Found: C 74.12; H 7.49; N 2.67.

EXAMPLE 8

20.0 g of trans-2,3-dihydro-2-(4-hydroxy-3-methoxyphenyl)-7-methoxy-3-methyl-5-(E)-propenylbenzofuran and 17.2 g of 2-isopropyl-3-ethyl-1,3-oxazolidine are held in 180 ml of absolute ethanol for 36 hours at 60° C. and subsequently the solvent and excess 2-isopropyl-1,3-oxazolidine are removed in vacuum. After purification by means of a chromatographic column there is obtained 10.6 g of N-(5-trans-2,3-dihydro-7-methoxy-3-methyl-5-(E)-propenyl-benzofuran-2-yl)-2-hydroxy-3-methoxyphenyl-(isopropyl)-methyl)-N-(2-hydroxyethyl)-N-ethylamine, a light brown oil.

$C_{28}H_{39}NO_5$ (469.39) Reported: C 71.58; H 8.39; N 2.98. Found: C 71.82; H 8.51; N 2.90.

EXAMPLE 9

20.0 g of trans-2,3-dihydro-2-(4-hydroxy-3-methoxyphenyl)-7-methoxy-3-methyl-5-(E)-propenylbenzofurane and 13.6 g of 3-allyl-1,3-oxazolidine are held in 240 ml of absolute alcohol for 48 hours at 70° C. and subsequently the solvent and excess 3-allyl-1,3-oxazolidine are removed in vacuum. After purification by means of a chromatographic column there is obtained 14.4 g of N-(5-(trans-2,3-dihydro-7-methoxy-3-methyl-5-(E)-propenyl-benzofuran-2-yl)-2-hydroxy-3-methoxyphenyl-methyl)-N-(2-hydroxyethyl)-N-allylamine, a colourless oil.

$C_{26}H_{33}NO_5$ (439.33) Reported: C 71.02; H 7.59; N 3.19. Found: C 70.92; H 7.61; N 3.16.

EXAMPLE 10

20.0 g of (1α, 2β, 3α)-1-ethyl-3-(4-hydroxy-3-methoxyphenyl)-6-methoxy-2-methyl-5-indanol and 31.9 g of 3,4-dimethyl-5-phenyl-1,3-oxazolidine are held in 250 ml of absolute alcohol for 60 hours at 70° C. and subsequently the solvent and excess 3,4-dimethyl-5-phenyl-1,3-oxazolidine are removed in vacuum. After purification by means of the chromatographic column there is obtained 8.9 g of N-(5-((1α, 2β, 3α)-1-ethyl-5-hydroxy-6-methoxy-2-methyl indan-3-yl)-2-hydroxy-3-methoxyphenyl-methyl)-N-(1-hydroxy-1-phenyl-2 propyl)-N-methylamine, a light brown oil.

$C_{31}H_{39}NO_5$ (505.39) Reported: C 73.61; H 7.79; N 2.77. Found: C 73.95; H 7.78; N 2.64.

EXAMPLE 11

20.0 g of trans-2,3-dihydro-2-(4-hydroxy-3-methoxyphenyl)-7-methoxy-3-methyl-5-(E)-propenylbenzofurane and 15.5 g of 3-butyl-1,3-oxazolidine are held in 180 ml of absolute alcohol for 36 hours at 70° C. and subsequently the solvent and excess 3-butyl-1,3-oxazolidine are removed in vacuum. After purification by means of a chromatographic column there is obtained 15.8 g of N-(5-(trans-2,3-dihydro-7-methoxy-3-methyl-5-(E)-propenyl-benzofuran-2-yl)-2-hydroxy-3-methoxyphenyl-methyl)-N-(2-hydroxyethyl)-N-butylamine, a colourless oil.

$C_{27}H_{37}NO_5$ (455.37) Reported: C 71.15; H 8.21; N 3.07. Found: C 71.25; H 8.15; N 3.00.

EXAMPLE 12

Production of 10 000 capsules with a content each of 100 mg of the active substance:
constituent compounds:

| | |
|---|---|
| N-(5-(trans-2,3-dihydro-7-methoxy-3-methyl-5-(E)-propenylbenzofuran-2-yl)-2-hydroxy-3-methoxy-phenylmethyl)-N-(2-hydroxyethyl)-N-methylamine | 1000 g |
| Lactose | 2,800 g |
| Talcum powder | 200 g |

Process:

The powdered constituents are screened with a screen 0.6 mm of mesh size. After that the effective substance is homegenised in a mixer at first together with the talcum powder and subsequently with lactose. On using a filling machine the gelatine capsules of suitable size are filled each with 400 mg of mixture.

EXAMPLE 13

Production of 10 000 ml of injection solution for filling into ampoules:
constituent compounds:

| | |
|---|---|
| N-(5-(trans-2,3-dihydro-7-methoxy-3-methyl-5-(E)-propenylbenzofuran-2-yl)-2-hydroxy-3-methoxyphenylmethyl)-N-(2-hydroxyethyl)-N-methyl ammonium chloride | 600 g |
| Sodium chloride | 10 g |
| Aqua pro injectione | ad 10 000 ml |

Process:

After dissolving the constituent compounds the solution is filtered through a glass filter plug of permeability G 3 and after that the ampoules are filled under nitrogen, for intravenous injections, of capacity 2 ml, and for use as additive to infusions into ampoules each 5 ml content

EXAMPLE 14

Production of 10 000 tablets each with a content of 50 mg of active substance:
constituent compounds:

| | |
|---|---|
| N-(5((1α, 2β, 3α)-1-ethyl-5-hydroxy-6-methoxy-2-methylindan-3-yl)-2-hydroxy-3-methoxyphenylmethyl)-N-(2-hydroxyethyl)-N-methylamine | 500 g |
| Lactose | 1700 g |
| Maize starch | 90 g |
| Polyethylene glycol 6000 | 90 g |
| Talcum powder | 90 g |
| Magnesium stearate | 30 g |

Process:

The powdered constituent compounds are screened with a screen of 0.6 mm of mesh size. Subsequently the active substance is mixed with the lactose, talcum powder, magnesium stearate and with half the quantity of starch in a suitable mixer. The other half of the starch is suspended in 50 ml of water and the suspension is added to a hot solution of polyethylene glycol at 80° in 190 ml. The paste obtained in this manner is added to the mixture of powdered constituent compounds and it is granulated, if necessary by adding further quantities of water. The granulated material is dried for 12 hours at 30°, passed through a screen of 1.2 mm mesh size and pressed into tablets of 7 mm diameter.

EXAMPLE 15

Production of 10 000 capsules with a content each of 50 mg of active substance:
Constituent compounds:

| | |
|---|---|
| N-(5-trans-2,3-dihydro-7-methoxy-3-methyl-5-(E)-propenyl-benzofuran-2-yl)-2-hydroxy-3-methoxyphenylmethyl)-N-(2-hydroxyethyl)-benzyl ammonium chloride | 500 g |
| Lactose | 2800 g |
| Talcum powder | 200 g |

Process:

After basically the same procedure as in example 12 the gelatine capsules are filled, by using a filling machine, of suitable size each with 350 mg of mixture.

EXAMPLE 16

Production of 10 000 tablets with a content each of 70 mg of active substance:
Constituent compounds

| | |
|---|---|
| N-(5-((1α, 2β, 3α)-1-ethyl-5-hydroxy-6-methoxy-2-methylindan-3-yl)-2-hydroxy-3-methoxyphenylmethyl-N-(2-hydroxyethyl)-N-butylamine | 700 g |
| Maize starch | 1000 g |
| Magnesium stearate | 90 g |
| Mannitol | 100 g |
| Microcrystalline silicic acid | 100 g |
| Lactose | 350 g |

Process:

In the same manner as in Example 14, the component compounds are screened and processed with water into a thick paste which is granulated and, after drying and screening, compacted into tablets.

We claim:

1. A process for manufacturing a compound of the formula

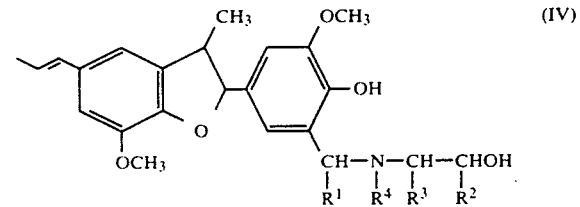

wherein
R$^1$ is selected from the group consisting of hydrogen, an unbranched or branched C$_1$–C$_4$ alkyl, halogen-substituted phenyl, and phenyl;
R$^2$ is hydrogen or phenyl;
R$^3$ is hydrogen or methyl; and
R$^4$ is selected from the group consisting of an unbranched or branched C$_1$–C$_4$ alkyl, an hydroxy-substituted unbranched or branched C$_1$–C$_4$ alkyl, allyl, and benzyl,
comprising reacting a dimer of isoeugenol of the formula

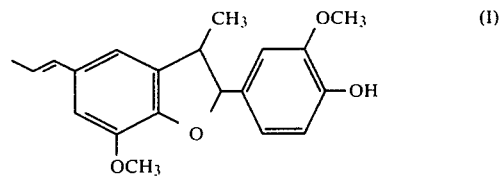

with an oxazoidine of the formula

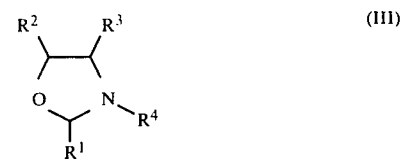

wherein R$^1$, R$^2$, R$^3$, and R$^4$ have the same meaning as above.

2. The process of claim 1, wherein the reaction is carried out in a solvent selected from the group consisting of methanol, ethanol, 2-propanol, diethyl ether, diisopropyl ether, dioxan, tetrahydrofuran, acetonitrile and propionitrile.

3. The process of claim 1 further comprising reacting a compound of formula (IV) with a therapeutically usable acid to form a therapeutically usable salt of the compound of formula (IV).

4. N-(5-(trans-2,3-dihydro-7-methoxy-3-methyl-5-(E)-propenyl-benzofuran-2-yl)-2-hydroxy-3-methoxy phenylmethyl)-N-(2-hydroxyethyl)-N-benzylamine and its therapeutically usable salts with acids.

5. N-(5-(trans-2,3-dihydro-7-methoxy-3-methyl-5-(E)-propenyl-benzofuran-2-yl)-2-hydroxy-3-methoxyphenylmethyl)-N-(1-hydroxy-1-phenyl-2-propyl)-N-methylamine and its therapeutically usable salts with acids.

6. N-(5(trans-2,3-dihydro-7-methoxy-3-methyl-5-(E)-propenyl-benzofuran-2-yl)-2-hydroxy-3-methoxyphenylmethyl)-N-(2-hydroxyethyl)-N-allylamine and its therapeutically usable salts with acids.

7. A pharmaceutical composition for protection against liver damage comprising a liver-damage protecting effective amount of a compound selected from the group consisting of N-(5-trans-2,3-dihydro-7-methoxy-3-methyl-5-(E)-propenyl-benzofuran-2-yl)-2-hydroxy-3-methoxy phenylmethyl)-N-(2-hydroxyethyl)-N-benzylamine, N-(5-trans-2,3-dihydro-7-methoxy-3-methyl-5-(E)-propenyl-benzofuran-2-yl)-2-hydroxy-3-methoxyphenylmethyl)-N-(1-hydroxy-1-phenyl-2-propyl)-N-methylamine, N-(5-trans-2,3-dihydro-7-methoxy-3-methyl-5-(E)-propenyl-benzofuran-2-yl)-2-hydroxy-3-methoxyphenylmethyl)-N-(2-hydroxyethyl)-N-allylamine, and a therapeutically usable salt thereof, and a pharmaceutically acceptable carrier.

* * * * *